US010854961B2

(12) United States Patent
Hartmann-Bax et al.

(10) Patent No.: US 10,854,961 B2
(45) Date of Patent: Dec. 1, 2020

(54) IMPLANTABLE ELECTRONIC MEDICAL DEVICE AND TRANSMIT/RECEIVE ANTENNA THEREFOR

(71) Applicant: BIOTRONIK SE & CO. KG, Berlin (DE)

(72) Inventors: Kathy Hartmann-Bax, Nuthe-Urstromtal (DE); Marina Ruschel, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 63 days.

(21) Appl. No.: 16/196,152

(22) Filed: Nov. 20, 2018

(65) Prior Publication Data

US 2019/0165458 A1 May 30, 2019

(30) Foreign Application Priority Data

Nov. 30, 2017 (EP) .................................... 17204670

(51) Int. Cl.
*H01Q 1/27* (2006.01)
*A61N 1/37* (2006.01)
*A61N 1/372* (2006.01)
*H01Q 1/36* (2006.01)
*H01Q 1/24* (2006.01)
(Continued)

(52) U.S. Cl.
CPC ......... *H01Q 1/273* (2013.01); *A61N 1/37229* (2013.01); *H01Q 1/14* (2013.01); *H01Q 1/24* (2013.01); *H01Q 1/36* (2013.01); *A61N 1/375* (2013.01); *H01Q 1/42* (2013.01); *H01Q 7/00* (2013.01); *H01Q 9/42* (2013.01)

(58) Field of Classification Search
CPC ............ H01Q 1/27; H01Q 1/273; H01Q 1/36; H01Q 9/42; A61N 1/372; A61N 1/37229
See application file for complete search history.

(56) References Cited

U.S. PATENT DOCUMENTS 7,317,946 B2    1/2008  Twetan et al.
2011/0082523 A1* 4/2011  Nghiem ............. A61N 1/37229
                                                      607/60
(Continued)

FOREIGN PATENT DOCUMENTS

EP        3028740 A1     6/2016
EP        2643050 B1     7/2016
WO     2016051206 A1     4/2016

*Primary Examiner* — Hoang V Nguyen
(74) *Attorney, Agent, or Firm* — Laurence A. Greenberg; Werner H. Stemer; Ralph E. Locher

(57) ABSTRACT

An implantable electronic medical device has a device body and a header placed thereon, and includes a telemetry assembly for signal transmission to and/or from outside the body of a patient when the device is implanted, in particular for the wireless bidirectional communication. A transmit/receive antenna, which is physically formed of an elongated conductor and arranged in the region of the header and which is configured so as to have a form fit with the outer contour of at least a portion of the header, and is fixed thereby in the header, is at least largely assigned to the telemetry assembly. A first section of the conductor has a spring elastic design and forms a bracket or clamp. The bracket embraces a connector in the header. There is also described a transmit/receive antenna of a telemetry assembly of an implantable electronic medical device.

14 Claims, 4 Drawing Sheets

(51) Int. Cl.
*H01Q 1/14* (2006.01)
*A61N 1/375* (2006.01)
*H01Q 9/42* (2006.01)
*H01Q 1/42* (2006.01)
*H01Q 7/00* (2006.01)

(56) References Cited

U.S. PATENT DOCUMENTS

2013/0116763 A1 5/2013 Parker et al.
2014/0364714 A1 12/2014 Ameri et al.

\* cited by examiner

IMPLANTABLE ELECTRONIC MEDICAL DEVICE AND TRANSMIT/RECEIVE ANTENNA THEREFOR

CROSS-REFERENCE TO RELATED APPLICATION

This application claims the priority, under 35 U.S.C. § 119, of European patent application EP 17204670.8, filed Nov. 30, 2017; the prior application is herewith incorporated by reference in its entirety.

BACKGROUND OF THE INVENTION

Field of the Invention

The invention relates to an implantable electronic medical device, comprising a device body and a header placed thereon, including a telemetry assembly for signal transmission to and/or from outside the body of a patient when the device is implanted, in particular for wireless bidirectional communication, wherein a transmit/receive antenna that is substantially formed spatially of an elongated conductor and arranged in the region of the header, is assigned to the telemetry assembly. The invention furthermore relates to a corresponding transmit/receive antenna.

It has been common practice for quite some time for implantable electronic medical devices to transmit measured values recorded in the body or state values of the device to outside the body of the patient, or to receive control or programming signals from outside, via short-range wireless communication links, so-called telemetry. As with any wireless connection, antennas are required for this communication. The antenna provided in the implantable device is seated outside the electromagnetically shielding device housing, which is to say at or in the region of a so-called header in the case of devices comprising such a header.

Like all components of implantable electronic medical devices, telemetry antennas are also the subject of continual development. Examples of modern antennas of this type are described in U.S. Pat. No. 7,317,946 B2 or European Patent EP 2 643 050 B1, for example. Both documents show the design of such antennas having a spiral or meander structure so as to increase the effective conductor length, while preserving the necessary compactness. Additionally, U.S. Pat. No. 7,317,946 B2 describes how a transmit/receive antenna of the type in question can be accommodated in the header of an implantable device in a space-saving manner and, at the same time, an advantageous antenna characteristic can be implemented.

United States patent application publication US 2014/0364714 A1 discloses various embodiments of antennas of implantable medical devices. Several antennas have a spiral-shaped structure.

Further implants comprising antennas are disclosed in the patent application documents US 2013/0116763 A1, EP 3 028 740 A1 and WO 2016/051206 A1.

SUMMARY OF THE INVENTION

It is an object of the invention to provide an improved implantable electronic medical device, and in particular a transmit/receive antenna for the telemetry function of such a device, wherein in particular low mounting complexity and accordingly low mounting costs are to be combined with advantageous electromagnetic properties.

With the above and other objects in view there is provided, in accordance with the invention, an implantable electronic medical device, comprising:

a device body, a header disposed on the device body, and a telemetry assembly for signal transmission to and/or from outside a body of a patient when the device is implanted;

a transmit/receive antenna connected to the telemetry assembly, the transmit/receive antenna being an elongated conductor arranged in a region of the header;

the transmit/receive antenna being configured to form-fittingly engage an outer contour of at least a portion of the header and to be fixed in the header;

the elongated conductor having a first section forming a bracket with a spring-elastic design configured to embrace a connector in the header.

In other words, according to one aspect, an implantable electronic medical device is disclosed, which comprises a device body and a header placed thereon. The device furthermore comprises a telemetry assembly for signal transmission to and/or from outside the body of a patient when the device is implanted, and in particular for wireless bidirectional communication. The telemetry assembly is assigned a transmit/receive antenna, which essentially is physically formed of an elongated conductor and arranged in the region of the header and which is configured so as to have a form fit with the outer contour of at least a portion of the header and to be fixed thereby in the header. A first section of the conductor is spring elastic and forms a bracket, wherein the bracket embraces a connector in the header.

The device can be an implantable cardiac pacemaker, an implantable cardioverter defibrillator (ICD) or an implantable sensor.

According to a further aspect, a transmit/receive antenna of a telemetry assembly of an implantable electronic medical device is provided. The device comprises a device body and a header placed thereon. The transmit/receive antenna is physically formed of an elongated conductor and configured so as to form a form fit with the outer contour of a portion of the header, and to be fixable thereby in the header. A first section of the conductor is spring elastic and forms a bracket, whereby the bracket can embrace a connector in the header.

According to the invention, the transmit/receive antenna is configured so as to have a form fit with the outer contour of at least a portion of the header, and to be fixed thereby on the header. It goes without saying that, in addition to the fixation referred to here, a connection also exist between an antenna end and a connection pin in the header, which can be designed, for example, as a weld, solder or conductive adhesive connection or, as an alternative, also as a crimp, plug or clamp connection, however which primarily serves to electrically connect the telemetry assembly and the antenna.

The spring elastic bracket enables particularly easy mounting by "clipping" the antenna onto the otherwise pre-assembled interior structure of the header, without the need for a tool and using a single fixation step. It moreover enables reliable fixation, even when minor component tolerances are present, and avoids handling errors during mounting.

A second section of the conductor can be arranged on an upper face of a connection block, wherein the connection block comprises the connector.

At least one connecting conductor, which is electrically conductively connected the connector, can be arranged on one side of the connection block. The at least one connecting conductor establishes an electrical connection between a plug introduced into the connector and electrical components in the device body.

The upper face of the connection block and the side of the connection block can include a substantially right angle (within the range of the manufacturing tolerances, for example 90° plus/minus 2° or 90° plus/minus 1°). Since a large portion of the antenna is arranged on the upper face of the connection block, the plane of the antenna does not intersect the plane in which the connecting conductor(s) is (are) arranged. In this way, the interactions between the antenna and the at least one connecting conductor with a magnetic field are optimized, and the magnetic resonance imaging (MRI) compatibility of the device is ensured.

The first section of the conductor can furthermore be angled with respect to the second section of the conductor, which is arranged on the upper face of the connection block. The first section and the second section can include a substantially right angle (within the range of the manufacturing tolerances, for example 90° plus/minus 2° or 90° plus/minus 1°).

It may be provided that the antenna comprises exactly one bracket by way of which the antenna is attached to the connection block. The "clipping" of the one (single) bracket to the connector, together with the arrangement of the majority of the antenna (second section of the conductor) on the upper face of the connection block enables sufficient attachment.

In a further embodiment, the elongated conductor forming the essential portion of the antenna structure is ribbon-shaped, and more particularly having a ratio of width to height of the ribbon-shaped conductor of 4:1 or more, and in particular more than 8:1. This design allows the antenna to be produced in a technologically particularly simple manner as a bent stamping from a suitable electrically conducting metal sheet or an electrically conducting metal foil and has a large radiation surface, in relation to the material use.

In addition to the design as a bent stamping, a variety of other designs of the antenna according to the invention are also possible, for example as a 3D printed sintered part or a metal injection molded (MIM) part, or also as a part formed of a suitable electrically conducting metal sheet or an electrically conducting metal foil using an ablation process.

So as to achieve an electromagnetically advantageous overall conductor length as well as simple producibility and mounting, the transmit/receive antenna in a further embodiment is arranged over the majority of the extension thereof in a meander-shaped progression in a plane on the upper face and/or on a lateral face of the header. In one embodiment of this design, reinforcement bridges are provided in the meander bends at least in a sub-section of the meander-shaped progression.

The bracket can be designed as an Ω-shaped bracket or clamp. This design is particularly suitable for a number of devices having header designs that have been tried and tested in practice, the structure of which includes substantially standardized connectors for electrode and/or sensor lines. In addition to good mechanical attachment of the antenna to the connection block, the Ω-shaped bracket also acts as an antenna. The radiation characteristic and the reception characteristic of the antenna are improved as a result of the Ω-shaped bracket. This also further improves the MRI compatibility of the device. For headers having a deviating configuration, the antenna design can advantageously be modified by an appropriately adapted shape of a functionally corresponding bracket section, or elastic hooks or the like may be provided.

The antenna according to the invention, at least in embodiments of the invention, allows in particular one or more of the advantages described hereafter to be achieved:

The antenna allows the entire header to be produced in an automated process and thus contributes to increasing the efficiency and lowering the costs in the production of the device.

As a result of a conductor length and radiation surface that have been optimized with respect to the material use and the mechanical properties, the antenna properties are optimized.

The form fit and the optional sectional elasticity of the antenna with respect to the header component contour essentially avoid undesirable performance-impairing deformations of the antenna during mounting, and thus substantially prevent complex rework and scrap.

Other features which are considered as characteristic for the invention are set forth in the appended claims.

Although the invention is illustrated and described herein as embodied in an implantable electronic medical device and transmit/receive antenna therefor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
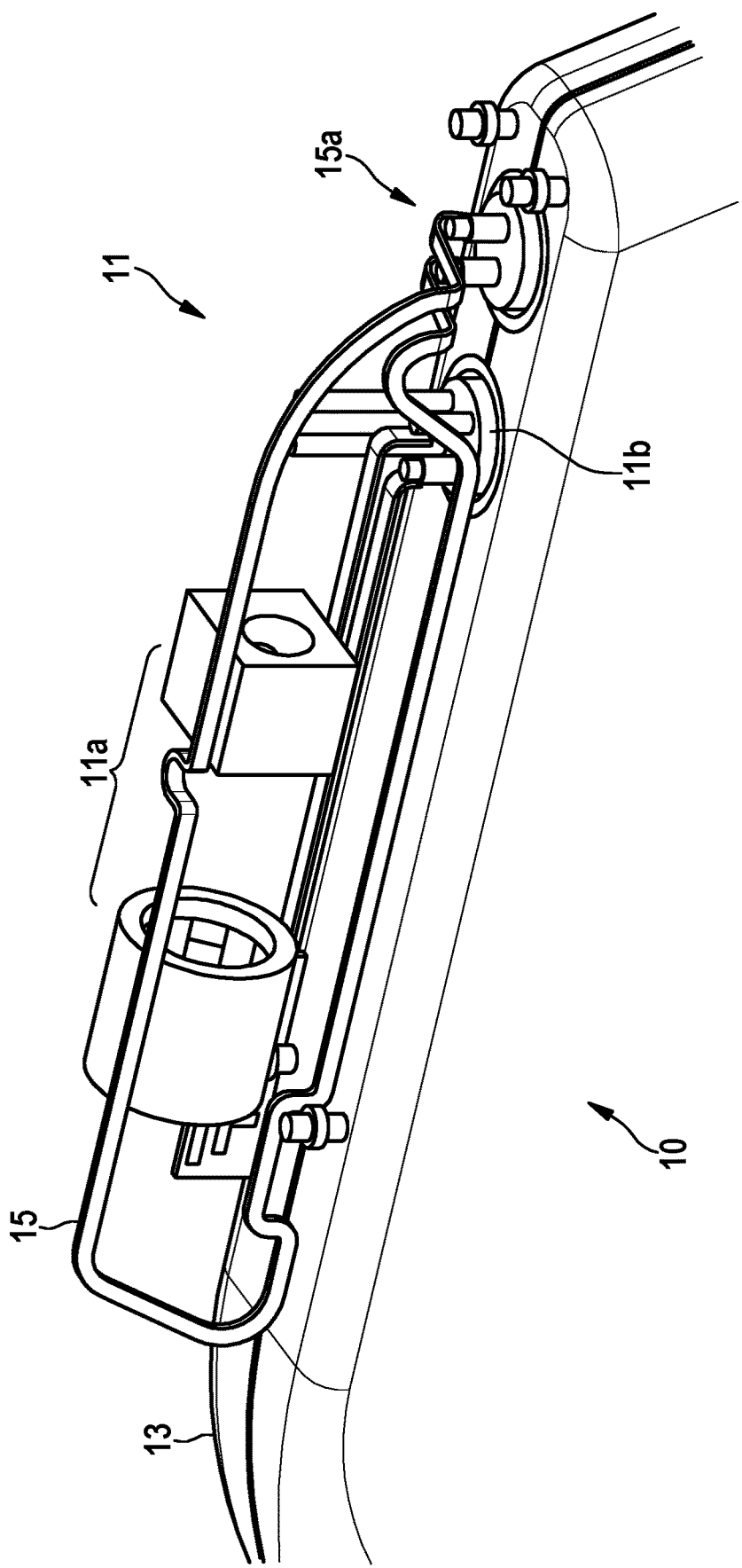
FIG. 1 shows a perspective view of a conventional transmit/receive antenna in the header of a single-chamber cardiac pacemaker.

Referring now to the figures of the drawing in detail and first, particularly, to FIG. 1 thereof, there is shown a detail illustration of a header 11 of a cardiac pacemaker 10 comprising connector components 11a and an associated connecting element 11b for the connection to electronic components in a housing 13 of the pacemaker. The figure furthermore shows a frame-like transmit/receive antenna 15 and a connecting element 15a assigned thereto. It is apparent that the frame-like transmit/receive antenna 15 is arranged in a substantially freely "floating" manner in the header 11 and only mechanically fixed to the connecting element 15a, which, of course, also serves the electrical connection thereof.

Figure 2:
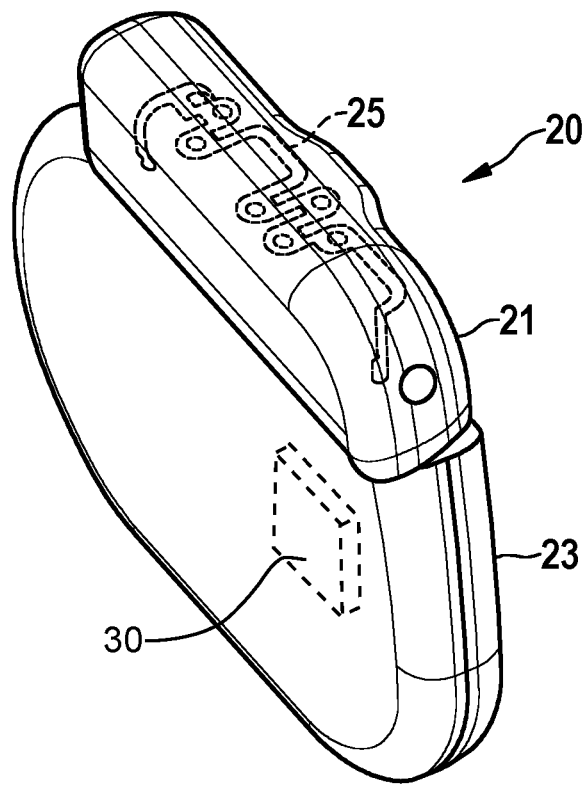
FIG. 2 shows a perspective overall view of a single-chamber cardiac pacemaker comprising an embodiment of the transmit/receive antenna shown therein.

FIG. 2 shows an outside view of a pacemaker 20 designed according to the invention, comprising a header 21 and a housing 23. A transmit/receive antenna 25 according to the invention is arranged in the header 21. The transmit/receive antenna 25 is shown in greater detail in FIG. 3, together with a connection block 21a, in a perspective illustration. There is also indicated, in dashed lines, a telemetry assembly 30 inside the device housing 23. The telemetry assembly is electrically connected to the transmit/receive antenna 25.

A first section 25.2 of the antenna 25 is angled with respect to a second section 27. The first section 25.2 and the second section 27 form a right angle. It is apparent that the antenna 25, over the majority of the extension thereof (second section 27), is located with a meander-shaped progression in a plane on the upper face 26 of the connection block 21a, and only the two end sections 25.1 and 25.2 thereof are located outside this plane. The end section 25.1 leads to the connecting element (not shown) for the connection to an associated telemetry assembly in the pacemaker housing. The first section 25.2 is designed as an Ω-shaped bracket 24, or a clamp 24, which embraces a (cylindrical, for example) connector 22 of the connection block 21a in an elastically resilient manner. It is also apparent that bridge-like connections are provided within the meander of the antenna progression, which bring about an increase in the flexural rigidity of the antenna structure. It is furthermore apparent that the transmit/receive antenna 25 is designed as a flat bent stamping or formed part. A connecting conductor 29, which has an electrical connection to the connector 22, is arranged on a side 28 of the connection block 21a. The upper face 26 of the connection block 21a and the side 28 of the connection block 21a include a right angle.

Figure 3:
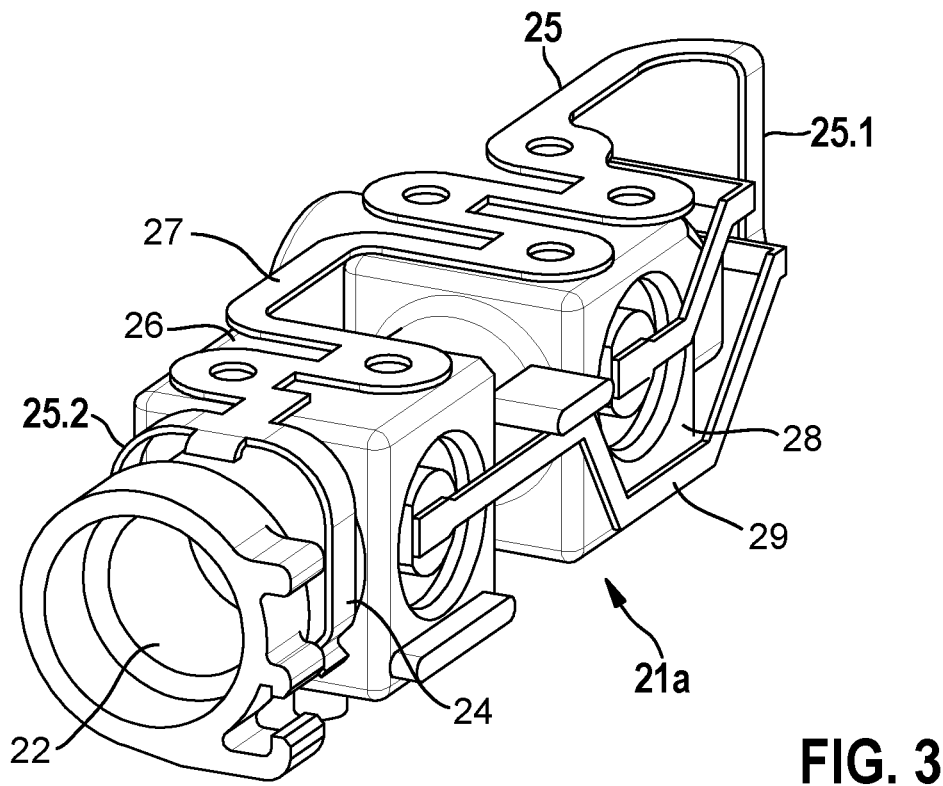
FIG. 3 shows a perspective detail illustration of the header structure comprising the transmit/receive antenna of the pacemaker according to FIG. 2.
Figure 4A:
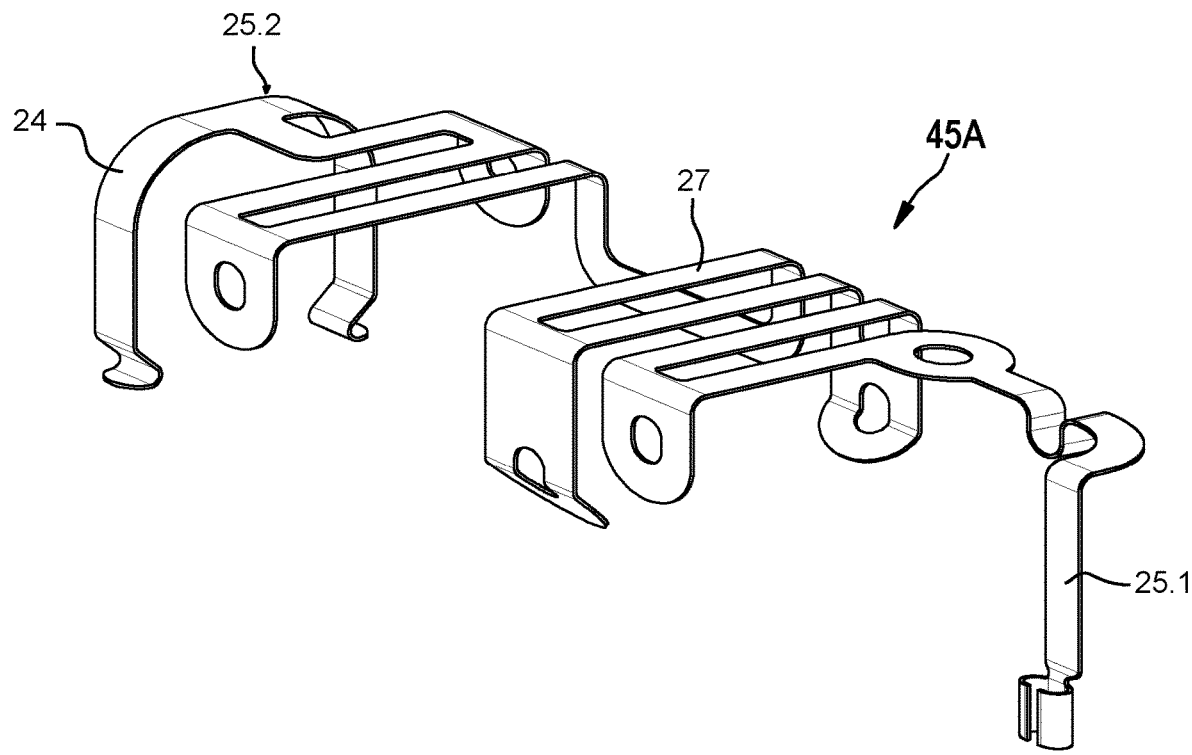
FIGS. 4A-4D show schematic perspective illustrations of further embodiments of the transmit/receive antenna.
Figure 4B:
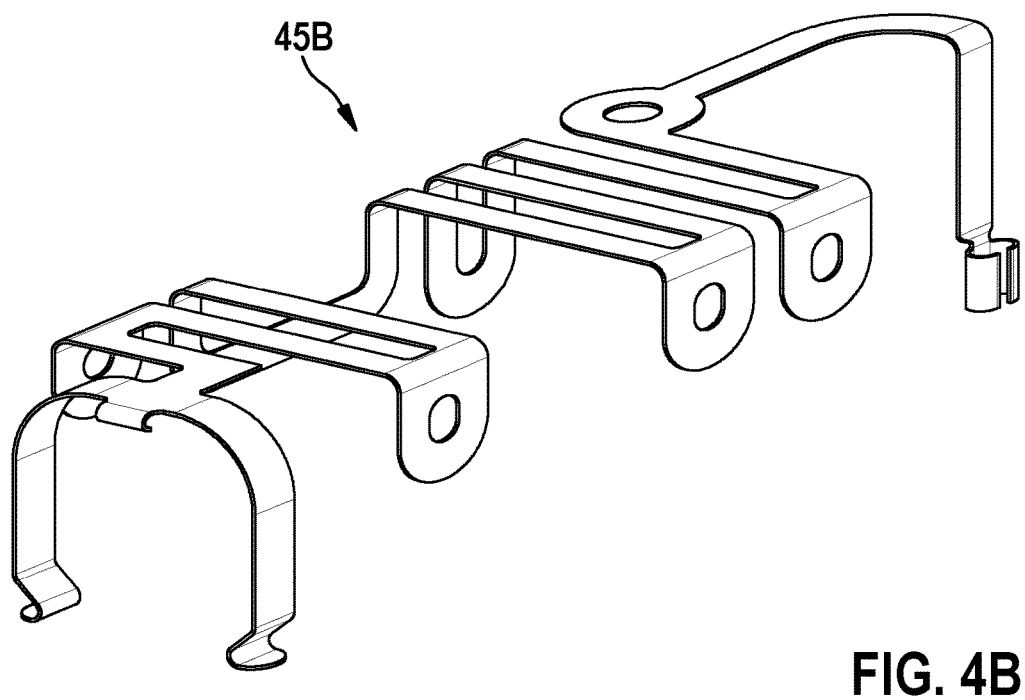
Figure 4C:
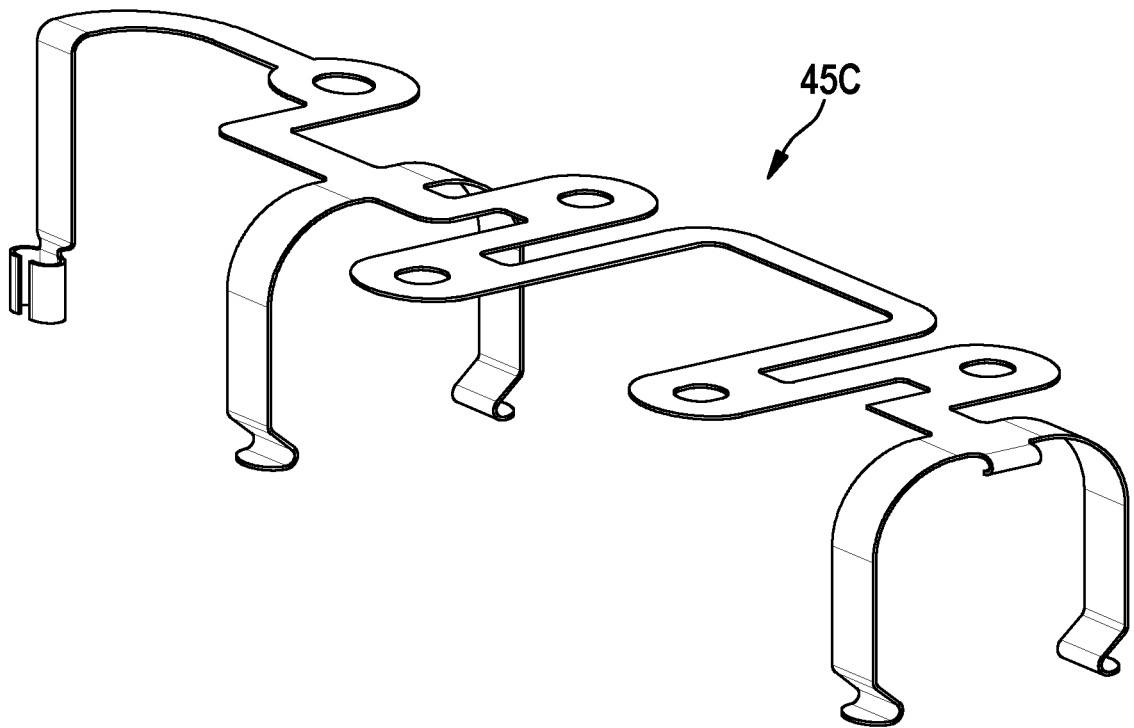
Figure 4D:
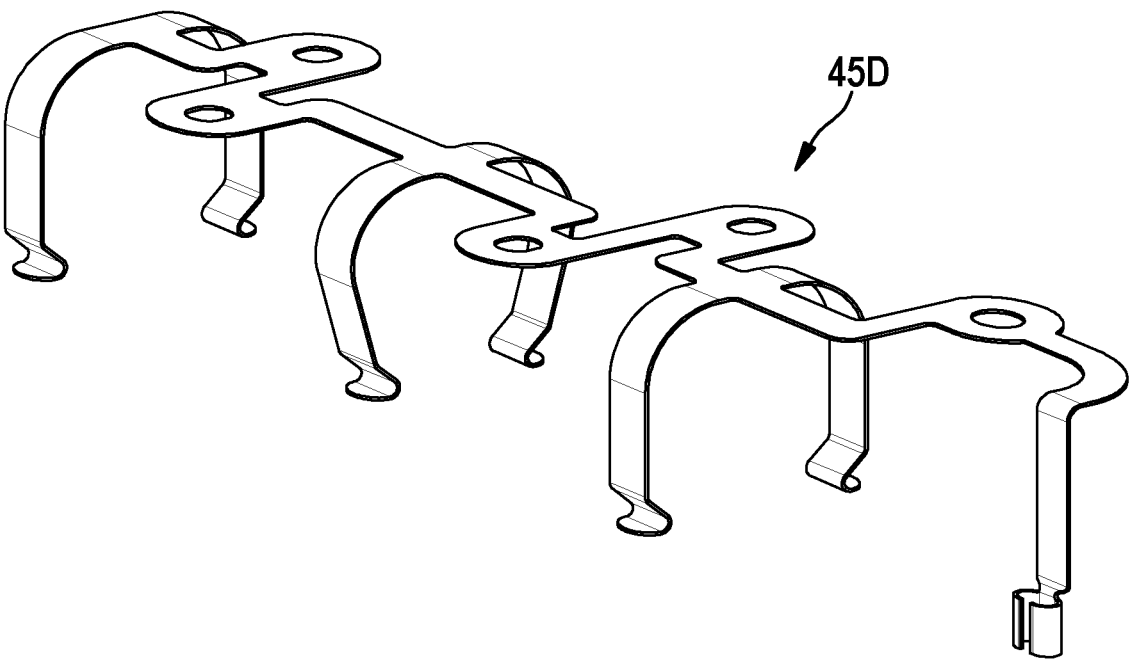

FIGS. 4A to 4D show further embodiments of transmit/receive antennas 45A to 45D. The parts corresponding to the first and second sections 25.1 and 25.2, and to the meander 27, of FIG. 3 are identified in FIG. 4A. In the antenna 45A according to FIG. 4A and the antenna 45B according to FIG. 4B, the respective end sections of the meanders of the antenna center section are bent at a right angle, whereby an additional form fit can be formed with a connector assembly (not shown) of the header located therebeneath in the assembled state. The transmit/receive antenna 45C according to FIG. 4C and the transmit/receive antenna 45D according to FIG. 4D each have more than one bracket section and thus, in the assembled state, fix the respective antenna in several locations by embracing a cylindrical section of the respective header assembly (not shown), which is located beneath the antenna, in an elastically resilient manner. It shall be pointed out that the bracket sections in all embodiments also have an electrical function, in addition to the mechanical fixation function, and advantageously influence the antenna characteristic.

In addition, the invention can also be implemented in a plurality of modifications of the examples shown here and of aspects of the invention that are pointed out above.

The invention claimed is:

1. An implantable electronic medical device, comprising:
a device body, a header disposed on said device body, and a telemetry assembly for signal transmission to and/or from outside a body of a patient when the device is implanted;
a transmit/receive antenna connected to said telemetry assembly, said transmit/receive antenna being an elongated conductor arranged in a region of said header;
said transmit/receive antenna being configured to form-fittingly engage an outer contour of at least a portion of said header and to be fixed in said header;
said elongated conductor having a first section forming a bracket with a spring-elastic design configured to embrace a connector in said header and a second section arranged on an upper face of a connection block in said header, said connection block comprising the connector.

2. The device according to claim 1, which comprises at least one connecting conductor, which has an electrically conductive connection with the connector, arranged on a side of said connection block.

3. The device according to claim 2, wherein said upper face of said connection block and said side of said connection block include a substantially right angle.

4. The device according to claim 1, wherein said first section of said conductor is angled with respect to said second section of said conductor, which is arranged on said upper face of said connection block.

5. The device according to claim 1, wherein said transmit/receive antenna is arranged in said second section of the conductor, and said transmit/receive antenna is formed with a meander-shaped progression arranged in a plane on said upper face of said connection block in a majority of an extension of said transmit/receive antenna.

6. The device according to claim 5, which comprises reinforcement bridges in meander bends at least in a subsection of said meander-shaped progression.

7. The device according to claim 1, wherein said elongated conductor is a ribbon-shaped conductor.

8. The device according to claim 7, wherein a ratio of a width to a height of said ribbon-shaped conductor is 4:1 or more.

9. The device according to claim 8, wherein the ratio is more than 8:1.

10. The device according to claim 1, wherein said transmit/receive antenna is a device selected from the group consisting of a bent stamping, a 3D printed sintered part, and a metal injection molded part.

11. An implantable electronic medical device, comprising:
a device body, a header disposed on said device body, and a telemetry assembly for signal transmission to and/or from outside a body of a patient when the device is implanted;
a transmit/receive antenna connected to said telemetry assembly, said transmit/receive antenna being an elongated conductor arranged in a region of said header;
said transmit/receive antenna being configured to form-fittingly engage an outer contour of at least a portion of said header and to be fixed in said header;
said elongated conductor having a first section forming an Ω-shaped bracket with a spring-elastic design configured to embrace a connector in said header.

12. A transmit/receive antenna of a telemetry assembly of an implantable electronic medical device, the medical device having a device body and a header disposed on said device body, the transmit/receive antenna comprising:
an elongated conductor configured to form a form fit with a outer contour of at least a portion of the header, and to be fixed thereby in the header;
said conductor having a first section with a spring elastic design forming a bracket configured to embrace a connector in the header and a second section, and wherein said first section of said conductor is angled with respect to said second section of said conductor.

13. A transmit/receive antenna of a telemetry assembly of an implantable electronic medical device, the medical device having a device body and a header disposed on said device body, the transmit/receive antenna comprising:

an elongated conductor configured to form a form fit with a outer contour of at least a portion of the header, and to be fixed thereby in the header;

said conductor having a first section with a spring elastic design forming an Ω-shaped bracket configured to embrace a connector in the header.

14. An implantable electronic medical device, comprising:

a device body, a header disposed on said device body, and a telemetry assembly for signal transmission to and/or from outside a body of a patient when the device is implanted;

a transmit/receive antenna connected to said telemetry assembly, said transmit/receive antenna being an elongated conductor arranged in a region of said header;

said transmit/receive antenna being configured to form-fittingly engage an outer contour of at least a portion of said header and to be fixed in said header; and said elongated conductor having a first section forming a bracket with a spring-elastic design configured to embrace a connector in said header with direct physical and electrical contact therewith.

* * * * *